United States Patent
Koltay et al.

(10) Patent No.: US 8,834,793 B2
(45) Date of Patent: Sep. 16, 2014

(54) APPARATUS AND METHOD FOR DISPENSING CELLS OR PARTICLES CONFINED IN A FREE FLYING DROPLET

(71) Applicant: Albert-Ludwigs-Universitaet Freiburg, Freiburg (DE)

(72) Inventors: Peter Koltay, Freiburg (DE); Azmi Yusof, Freiburg (DE)

(73) Assignee: Albert-Ludwigs-Universitaet Freiburg, Freiburg (DE)

( * ) Notice: Subject to any disclaimer, the term of this patent is extended or adjusted under 35 U.S.C. 154(b) by 0 days.

(21) Appl. No.: 13/707,086

(22) Filed: Dec. 6, 2012

(65) Prior Publication Data

US 2013/0095469 A1  Apr. 18, 2013

Related U.S. Application Data

(63) Continuation of application No. PCT/EP2010/058170, filed on Jun. 10, 2010.

(51) Int. Cl.
| | | |
|---|---|---|
| G01N 33/00 | (2006.01) | |
| B01L 3/00 | (2006.01) | |
| B41J 2/135 | (2006.01) | |
| C12M 1/36 | (2006.01) | |
| F04B 19/00 | (2006.01) | |
| B41J 2/045 | (2006.01) | |
| G01N 15/14 | (2006.01) | |
| G01N 35/10 | (2006.01) | |

(52) U.S. Cl.
CPC ......... *C12M 41/48* (2013.01); *G01N 2015/149* (2013.01); *G01N 2035/1041* (2013.01); *G01N 15/1404* (2013.01)

USPC .............. 422/73; 347/46; 347/68; 422/502; 422/505

(58) Field of Classification Search
USPC ............................................. 422/73
See application file for complete search history.

(56) References Cited

U.S. PATENT DOCUMENTS 3,380,584 A * 4/1968 Fulwyler .......................... 209/3
3,924,947 A * 12/1975 Hogg .............................. 356/39

(Continued)

FOREIGN PATENT DOCUMENTS

| DE | 197 06 513 A1 | 8/1998 |
| EP | 0 421 406 A2 | 4/1991 |

(Continued)

OTHER PUBLICATIONS

Official Communication issued in International Patent Application No. PCT/EP2010/058170, mailed on Mar. 23, 2011.

(Continued)

*Primary Examiner* — Jill Warden
*Assistant Examiner* — Brittany Fisher
(74) *Attorney, Agent, or Firm* — Keating & Bennett, LLP

(57) ABSTRACT

An apparatus for dispensing one or more cells or particles confined in a free flying droplet has a droplet generating device configured to eject out of an orifice a free flying droplet of a suspension of cells or particles. The droplet generating device has a branch-less one-way channel having the orifice at one end thereof. A device for detecting information on cells or particles located in an observation volume of the suspension within the branch-less one-way channel is provided. An ejected droplet is directed to a first position or a second position depending on the detected information.

21 Claims, 6 Drawing Sheets

(56) References Cited

U.S. PATENT DOCUMENTS

| | | | | |
|---|---|---|---|---|
| 4,009,435 | A | * | 2/1977 | Hogg .......................... 324/71.1 |
| 4,318,480 | A | * | 3/1982 | Lombardo et al. ............. 209/3.1 |
| 4,667,830 | A | * | 5/1987 | Nozaki et al. ................. 209/3.1 |
| 7,051,654 | B2 | | 5/2006 | Boland et al. |
| 7,294,249 | B2 | * | 11/2007 | Gawad et al. ................. 204/547 |
| 7,738,101 | B2 | * | 6/2010 | Mavliev ........................ 356/336 |
| 8,162,149 | B1 | * | 4/2012 | Perroud et al. ................ 209/631 |
| 2008/0286751 | A1 | | 11/2008 | Renaud et al. |
| 2009/0208577 | A1 | | 8/2009 | Xu et al. |

FOREIGN PATENT DOCUMENTS

| | | |
|---|---|---|
| GB | 1 485 284 A | 9/1977 |
| GB | 1 555 091 A | 11/1979 |
| WO | 2010/004627 A1 | 1/2010 |

OTHER PUBLICATIONS

Shapiro, "Microbial Analysis at the Single-Cell Level: Tasks and Techniques," Journal of Microbiological Methods, vol. 42, pp. 3-16, 2000.

Xu et al., "Inkjet Printing of Viable Mammalian Cells," Biomaterials, vol. 26, pp. 93-99, 2005.

Moon et al., "Layer by Layer Three-Dimensional Tissue Epitaxy by Cell-Laden Hydrogel Droplets," Tissue Engineering Part C: Methods, vol. 15, pp. 1-10, 2009.

Iwasaki et al., "Biocompatible Inkjet Printing Technique for Designed Seeding of Individual Living Cells," Tissue Engineering, vol. 11, pp. 1658-1666, 2005.

Tornay et al., "Electrical Detection and Ejection of Beads in a One-Cell-Per-Drop Microdispenser," 14th International Conference on Solid-State Sensors, Actuators and Microsystems, pp. 695-698, 2007.

Demirci et al., "Single Cell Epitaxy by Acoustic Picolitre Droplets," Lab on a Chip, vol. 7, pp. 1139-1145, 2007.

Cheung et al., "Impedance Spectroscopy Flow Cytometry: On-Chip Label-Free Cell Differentiation," Cytometry Part A, vol. 65A, pp. 124-132, 2005.

\* cited by examiner

APPARATUS AND METHOD FOR DISPENSING CELLS OR PARTICLES CONFINED IN A FREE FLYING DROPLET

CROSS-REFERENCE TO RELATED APPLICATIONS

This application is a continuation of copending International Application No. PCT/EP2010/058170, filed Jun. 10, 2010, which is incorporated herein by reference in its entirety.

BACKGROUND OF THE INVENTION

The present invention relates to an apparatus and method for dispensing cells or particles confined in a free flying droplet, and in particular, to an apparatus and method appropriate for dispensing and/or printing a precisely defined number of cells or particles confined in a free flying droplet.

According to the state of the art, single cells can be detected, manipulated, and in particular, be sorted by means of flow cytometry (FCM). Flow cytometry is described by H. M. Shapiro, "Microbial analysis at the single-cell level: tasks and techniques, "*Journal of Microbiological Methods*, vol. 42, pp. 3-16, 2000. Flow cytometry is an established technology provided by various commercial companies and applied in many applications. Generally, a flow cytometer has five main components, a flow cell enabling a liquid stream, a measuring system, a detector and an analog-to-digital conversion (ADC) system, an amplification system and a computer for analysis of the signals. The flow cell enabling the liquid stream may use a sheath fluid and carries and aligns the cells so that they pass single file, i.e. one by one, through a light beam for sensing. The measuring system commonly uses measurement of impedance or conductivity or makes use of optical systems. Commonly used optical systems may comprise lamps (mercury, xenon), high-power water-cooled lasers (such as argon, krypton or dye lasers), low-power air-cooled lasers (such as argon lasers at a wavelength of 488 nm, red-HeNe lasers at a wavelength of 633 nm, green-HeNe lasers or HeCd lasers (UV)), diode lasers (blue, green, red, violet) for providing light signals. The detector and analog-to-digital conversion system generates Forward Scatter (FSC), Side Scatter (SSC) as well as fluorescence signals from light and converts them into electrical signals that can be processed by a computer. The amplification system may be linear or logarithmic.

FCM enables separation and sorting of single cells according to specific optical properties at high throughput. However, FCM is not able to deal with a very small sample volume (such as from 1 to 10 µl), because stationary flow conditions have to be established inside the cytometer. For the same reason, FCM cannot deliver a defined number of living cells in a small liquid aliquot with a volume of 100 nl or below. The sorting mechanism of FCM relies on a stationary flow inside the flow cell that cannot be switched on and off in a sufficiently short time.

There are also efforts in the art to miniaturize FCM into a smaller and more compact size. Lab on a chip (LOAC) flow cytometers (LOAC-FCM) were introduced which aim to provide a relatively low cost, small and compact FCM. Reference is made to K. Cheung, S. Gawad, and P. Renaud, "Impedance spectroscopy flow cytometry: On-chip label-free cell differentiation," Cytometry Part A, vol. 65A, pp. 124-132, 2005 and U.S. Pat. No. 7,294,249 B2. U.S. Pat. No. 7,294,249 B2 discloses a microfluidic component and method in a fluid using a substrate having a channel for leading through individual particles for sorting particles in a fluid flow, in particular in a liquid flow. The component comprises a preparation area to specifically influence and separate the particles by means of dielectrophoresis, a measuring channel area having at least two sensing areas arranged in series with respect to the fluid flow direction, and a sorting area having electrode devices for sorting particles identified in the measuring channel area. Thus, U.S. Pat. No. 7,294,249 B2 discloses a miniaturized device for analyzing, counting an sorting cells or particles which do not need a labeling of cells. However, FCM technologies—whether standard or miniaturized—do not facilitate to locate selected cells or particles for advanced applications like single cell arrays or cell printing and are to be considered as continuous methods.

Recently, inkjet printing technology has been exploited to deliver living cells instead of inks for locating cells precisely into desired patterns, see T. Xu, J. Jin, C. Gregory, J. J. Hickman, and T. Boland, "Inkjet printing of viable mammalian cells," *Biomaterials*, vol. 26, pp. 93-99, 2005, and S. Moon, S. K. Hasan, Y. S. Song, F. Xu, H. O. Keles, F. Manzur, S. Mikkilineni, J. W. Hong, J. Nagatomi, E. Haeggstrom, A. Khademhosseini, and U. Demirci, "Layer by Layer Three-dimensional Tissue Epitaxy by Cell-Laden Hydrogel Droplets," *Tissue Engineering Part C: Methods*, vol. 16, pp. 157-166, 2010. In addition, reference is made to US 2009/0208577 A1. Inkjet printing technology enables much smaller volumes of aliquots, and at the same time, spatial resolved printing of cells confined in the droplets. Several applications have been demonstrated using this technology, especially in constructing artificial tissues or organs, arraying cells for high throughput cell screening in drug discovery, basic cell study and analysis. Inkjet printing technology confines cells in a liquid volume which is jetted in the form of a droplet in-flight, such that it offers a non-invasive or minimally invasive cell manipulation technique. Although the concept of printing cells suspended in free flying droplets has been presented before, the number of cells per droplet is generally random, see U. Demirci and G. Montesano, "Single cell epitaxy by acoustic picolitre droplets," *Lab on a Chip*, vol. 7, pp. 1139-1145, 2007.

US 2008/0286751 A1 discloses a dispensing device for microfluidic droplets especially for cytometry. A main microchannel extends between two first and second tanks and a homogenous or heterogeneous cellular suspension passes through the main micro-channel. A second micro-channel crosses the main micro-channel and comprises an ejection orifice. Upon generating a pressure wave in the second channel, a droplet may be ejected via the ejection orifice. Impedance measurements and/or optical analysis are used to measure properties of cells circulating in the main micro-channel. Cells or particles are identified according to pertinent characteristics, detected electrically and/or optically, in particular by criteria of size, cytoplasmic conductivity and/or membrane capacitance. Depending on the measurement results, the device can be programmed for parametering an ejection device case by case. When a particle which verifies specific criteria is detected, a pressure pulse is applied to the second channel and a droplet is ejected via the ejection orifice.

According to US 2008/0286751 A1, the cells or particles are supplied in a main channel, while the ejection orifice is arranged in a second channel. Thus, the cells or particles are supplied in a stream perpendicular to the dispenser opening, which needs additional microfluidic flow focusing elements and external flow control equipment like high precision pumps. This enhances the complexity of the whole apparatus and needs considerable volumes of cell suspension to prime the complete apparatus. The cross-flow in close vicinity of the orifice furthermore leads to the drawback that the orifice design is compromised with respect to the droplet generation process. In particular, the liquid volume enclosed between the orifice and the pressure source applied for actuation is larger than for most other dispensing devices according to the state of the art, and the cross-flow channels do provide additional escape paths for liquid to be expelled out of the orifice. The design requirements for the cross-flow design are therefore contradictory to an optimum orifice design for precise and efficient generation of small droplets.

Beside the standard technology cited above, M. Nakamura, A. Kobayashi, F. Takagi, A. Watanabe, Y. Hiruma, K. Ohuchi, Y. Iwasaki, M. Horie, I. Morita, and S. Takatani, "Biocompatible Inkjet Printing Technique for Designed Seeding of Individual Living Cells," *Tissue Engineering*, vol. 11, pp. 1658-1666, 2005, and R. Tornay, V. Chapuis, V. Haguet, F. Chatelain, and P. Renaud, "Electrical Detection and Ejection of Beads in a One-Cell-Per-Drop Microdispenser," presented at Solid-State Sensors, Actuators and Microsystems Conference, 2007, TRANSDUCERS 2007, International, 2007, also disclose producing micro droplets from a supplied cell suspension.

Inkjet printing of viable cells is disclosed in U.S. Pat. No. 7,051,654 B2. U.S. Pat. No. 4,318,480 relates to a method and apparatus for positioning a point of droplet formation in a jetting fluid of an electrostatic sorting device. Finally, DE 197 06 513 relates to a micro dosing device using a pressure chamber and a flexible membrane adjacent the pressure chamber.

SUMMARY

The present invention provides for an apparatus for dispensing one or more cells or particles confined in a free flying droplet, comprising:
a piezo driven on-demand droplet generating device configured to eject out of an orifice a free flying droplet of a suspension of cells or particles, the droplet generating device comprising a branch-less one-way channel having the orifice at one end thereof;
a device for detecting information on cells or particles located in an observation volume of the suspension within the branch-less one-way channel; and
director for directing an ejected droplet to a first position or a second position depending on the detected information.

Embodiments of the invention provide for a method for dispensing one or more cells or particles confined in a free flying droplet, comprising:
filling a piezo driven on-demand droplet generating device with a suspension comprising cells or particles, the droplet generating device comprising a branch-less one-way channel having an orifice at one end thereof;
detecting information on cells or particles located in an observation volume of the suspension device within the branch-less one-way channel; and
ejecting a droplet out of the orifice to a first or second position depending on the detected information.

Embodiments of the invention provide for program product comprising program code executable on a computing device, wherein the program code is effective to derive the information on the cells or particles from an output of a sensor device and to control an apparatus as mentioned above to direct an ejected droplet to the first position or the second position depending on the detected information.

Embodiments of the invention are based on the recognition that a desired number of cells or particles can be dispensed confined in a free flying droplet in a reliable manner by detecting information on cells or particles within an observation volume arranged in a branch-less one-way channel, a downstream end of which represents the orifice. Thus, the present application permits for a simple design of a droplet generating device while, at the same time, a desired number of cells or particles can be dispensed with high reliability.

In embodiments of the invention, the first position may be a target position and the second position may be a waste position or vice versa.

The term "branch-less one-way channel" is intended to mean a channel having a single inlet and a single outlet without any branching, so that a fluid entering the one-way channel at the inlet, in normal operation, leaves the one-way channel through the outlet. According to embodiments of the invention, the orifice out of which the free flying droplets are ejected forms the outlet of the one-way channel.

According to embodiments of the invention, the droplet generating device is controlled to eject out of the orifice free flying droplets repeatedly, wherein the free flying droplet is directed to a first position in case the detected information indicates that the suspension within the observation volumes fulfills a predetermined condition, while the free flying droplet is directed to a second position if this is not the case. In embodiments of the invention, the predetermined condition is that just one cell or particle is arranged within the observation volume.

Accordingly, embodiments of the invention permit for separation, sorting and non-contact printing of a defined number of cells, such as living biological cells and/or particles. In embodiments of the invention, the free flying droplets may be micro droplets having a volume of a few microliter or below, such as less than 1 µl, or even less such as several hundreds of picoliters. Embodiments of the invention permit for dispensing particular single cells confined in such droplets by a drop-on-demand droplet generation process. Embodiments of the invention enable inkjet-like printing of single individual cells on arbitrary substrates for numerous applications ranging from basic research to tissue engineering.

Embodiments of the invention overcome the shortcomings of standard technology by providing a droplet dispensing device supplied with a cell solution or particle solution and a measuring means that detects cells or particles inside the dispensing device close to the orifice. Embodiments of the invention provide an approach to produce droplets-on-demand containing one cell only that can be printed inkjet-like onto arbitrary substrates.

Embodiments of the invention are directed to an apparatus and method for encapsulating single living cells or particles into a micro-, nano- or picoliter sized liquid droplet. This liquid droplet bearing a single-cell or a single particle may be jetted from the orifice of a droplet generator in the form of a free flying droplet to enable inkjet-like printing of single-cells or particles. By the use of such embodiments of the invention, single-cells or single particles can be separated and aliquots of a precisely defined number of cells can be produced.

Embodiments of the invention provide for a method to sort a heterogeneous mixture of cells/particles according to their specific properties. By this sorting feature in combination with the inkjet-like printing capability, embodiments of the invention can overcome many limitations of the current FCM technology in the low volume and low cell number range described above.

Accordingly, embodiments of the present invention fulfills the long failed need in the art for an approach able to dispense one single cell or particle per printed droplet, for a droplet volume significantly smaller than 1 µl, for example, with high reliability. Contrary to known FCM technologies, which have to be considered as continuous cell sorting and separation technologies, embodiments of the invention enable on-demand cell or particle sorting and printing and can deal with very small volumes of cell suspension. Thus, embodiments of the invention not only provide for the capability to separate and sort living cells, but in addition the opportunity for "on-demand" supply of individual cells. This means that a defined number of cells/particles (such as 1 to N) can be delivered in an aliquot of liquid. In addition, embodiments of the invention enable to produce aliquots much smaller than achievable with FCM down to a volume range of several hundred picoliters and below. Moreover, according to embodiments of the invention, cells such as living cells, or particles are encapsulated in free flying droplets such that they can be printed onto substrates in a drop-on-demand and non-contact fashion.

The invention described here overcomes the drawbacks of US 2008/0286751 A1—namely the requirement for external flow control elements for the cross channel flow and the use of one specific pressure driven device with the described weakness regarding droplet generation—by enabling the use of "arbitrary" droplet generating devices exhibiting branchless one-way channels from which the droplets are expelled.

BRIEF DESCRIPTION OF THE DRAWINGS

For a detailed description of exemplary embodiments of the invention, reference will now be made to the accompanying drawings in which.

DETAILED DESCRIPTION OF THE INVENTION

Figure 1:
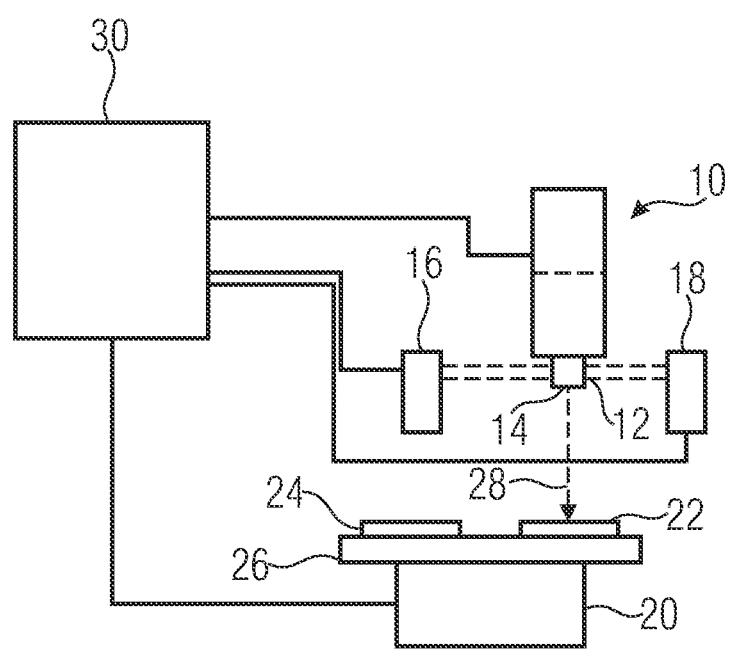
FIG. 1 is a schematic overview of an embodiment of the invention.

FIG. 1 shows an embodiment of an apparatus for dispensing one or more cells or particles confined in a free flying droplet. The apparatus comprises a droplet generating device 10 comprising a branch-less one-way channel 12 having an orifice or opening 14 at one end thereof. The apparatus further comprises a device 16, 18 for detecting information on cells or particles located in an observation volume of a suspension within the branch-less one-way channel 12. Means 20 for directing an ejected droplet to a first position 22 or a second position 24 depending on the detected information are provided.

According to the embodiment shown in FIG. 1, the first position 22 and the second position 24 are provided on a common carrier 26, wherein means 20 for directing an ejected droplet to the first position 22 or the second position 24 comprise a mechanical stage configured to move the common carrier 26 relative to the orifice 14 so that an ejected droplet (indicated by an arrow 28) may be directed to the first position 22 or the second position 24. Such means for directing are shown in FIG. 1 for exemplary purposes only and may be replaced by any other suitable means such as those described herein with respect to FIGS. 5a to 8b.

A controller 30 is provided to control the operation of the apparatus, and to this end, is connected to the droplet generating device 10, the device 16, 18 for detecting information, and the means 20 for directing. The first position may be a target position and the second position may be a waste position or vice versa.

In operation, the droplet generating device 10 is filled with a suspension comprising cells, such as living cells or particles, in such manner as to form a meniscus at the orifice 14. Thereupon, information on cells or particles located in the branch-less one-way channel 12 are detected, such as by an optical sensor comprising a light source 16 and an optical detector 18. The detected information may comprise at least one of presence, number and property of the cells/particles located in the observation volume. Depending on the detected information, means 20 for directing are controlled to align either first position 22 or second position 24 with the orifice 14. Thereupon, the fluid generating device 10 is actuated to eject a free flying droplet which is either directed to the first position 22 or the second position 24.

In embodiments of the invention, the droplet generator 10 may be a state of the art droplet generator to produce micro droplets from a supplied cell suspension. The droplet generation device can be an inkjet device, a piezo dispenser or any other suitable droplet generator as described in the documents of standard technology cited in the introductory portion, for example. In embodiments of the invention, without loss of generality, the droplet generator may work according to the principle described in DE 197 06 513 A1, the U.S. equivalent of which, U.S. Pat. No. 6,280,14B1, is incorporated herein by reference in its entirety.

In order to control the number of cells per droplet, embodiments of the present invention make use of a device 16, 18 for detecting the status of the cell suspension close to the orifice 14 inside the droplet generator 10. In embodiments of the invention, this detector device may be a laser source 16 and a photodiode 18 as shown in FIG. 1. In alternative embodiments, the measuring device may be implemented by an impedance sensor, such as disclosed in US 2008/0286751 A1, for example. In other embodiments, the device for detecting may be implemented making use of an optical camera. Basically, any device for detecting or measuring means is applicable that can determine information on cells/particles within the observation volume, such as the status of the cell suspension inside the droplet generator in terms of at least one of number, size, position, type, color, or any other property of the cells/particles inside the observation volume of the droplet generator. In embodiments of the invention, the device for detecting may be formed by an optical camera with suitable magnification lenses to deliver images of the cells/particles inside the droplet generator, so that properties of cells or particles located in the observation volume of the suspension can be derived making use of known image processing techniques. In particular, the camera (or in a general case, the device for detecting) observes the observation volume, i.e. a region of interest, close to the orifice. There are various ways to select and define the region of interest. In embodiments of the invention, the region of interest, and therefore, the observation volume, can be defined by the liquid volume that will be expelled from the droplet generator with the subsequent dispensing process. The region of interest can be larger, but should not be smaller than this volume to enable good performance. For a particular droplet generating device, the shape, size and position of the region of interest can be determined by experiments or numerical simulations. The region of interest may be defined so that any cell/particle residing in the region of interest will be ejected out of the orifice when a droplet is generated. Therefore, the output of the device for detecting, such as the camera, can be used to predict how many (0 to N) cells will be ejected by the next droplet dispensing event.

Figure 2:
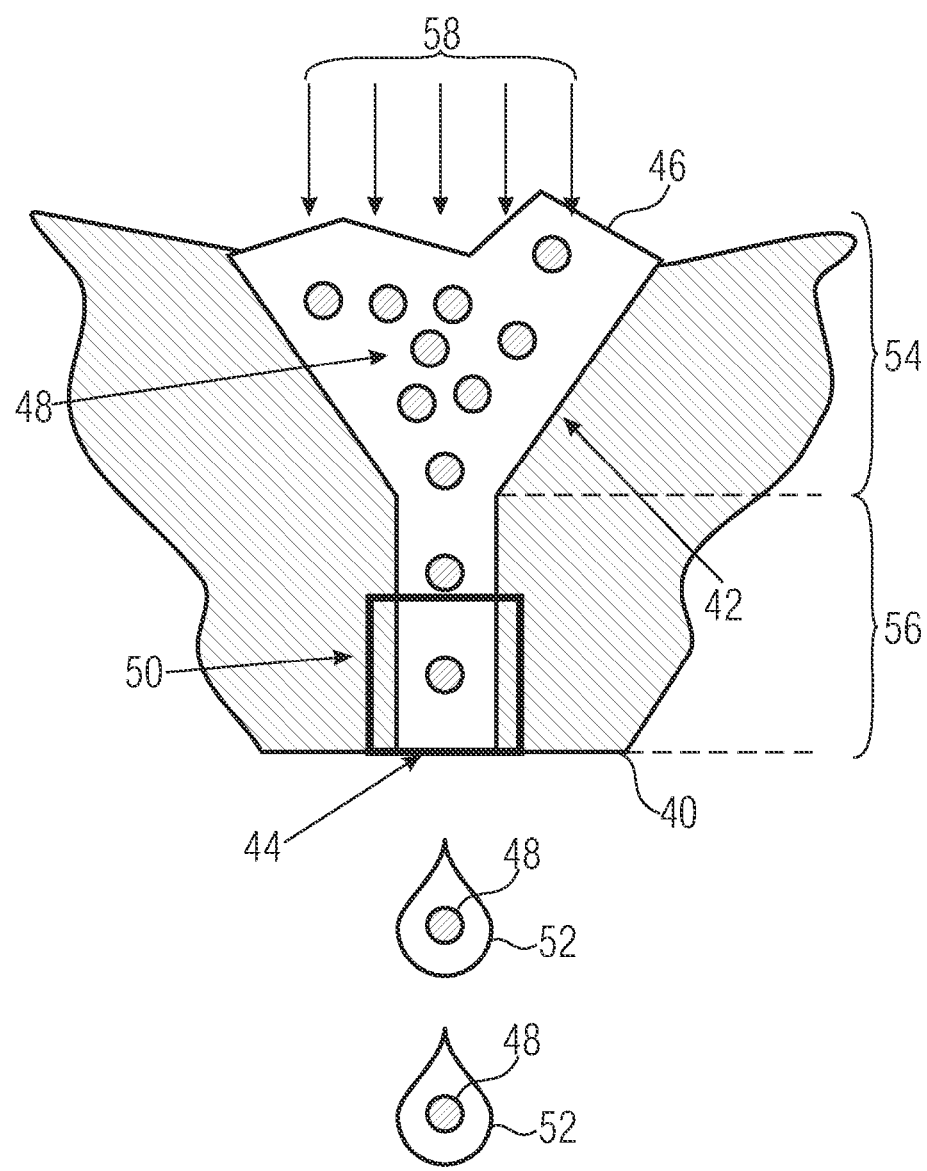
FIG. 2 is a schematic view of an embodiment of an output portion of a droplet generating device.

FIG. 2 shows an output portion 40 of a droplet generating device comprising a fluidic channel 42 and an orifice 44. The fluidic channel 42 is filled with a suspension 46, such as a buffer suspension, comprising cells 48, such as living cells. A region of interest (or observation volume) 50 is indicated in FIG. 2. Moreover, ejected free-flying liquid droplets 52 encapsulating single cells 48 are shown in FIG. 2. As it is shown in FIG. 2, the fluidic channel 42 comprises a fluid flow focusing section 54 and a single-cell detection section 56. A device for detecting (not shown in FIG. 2) is configured to detect information on cells, such as the presence of cells, within the single-cell detection section, and to be more specific, within the region of interest 50. The single-cell detection section 56 represents a branch-less one-way channel, which a cell suspension flow indicated by arrows 58 enters from the top. The fluidic channel 42 may be filled by capillary forces, gravity, or if needed, any other additional pressure means. The fluidic channel 42 may be connected to a fluidic reservoir to refill the fluidic channel 42 upon ejection of droplets from the orifice 44.

As it is clear from FIG. 2, the observation volume is within the portion of the cell suspension 46, which is located in the branch-less one-way channel 56.

Of course, the region of interest can also be defined in a different way by considering the size and position of the cells/particles in a more sophisticated fluid dynamic model of the droplet generating process, such as by CFD simulations. More sophisticated models may allow for a more precise determination of the number of cells/particles that will be expelled from the orifice with the subsequent droplet dispensing process. Such models may make use of the flow profile inside the droplet generator in the vicinity of the orifice to estimate the position, size, shape and location of the region of interest. For the sake of simplicity, a definition of the region of interest as shown in FIG. 2 will be used in the following as an example. In embodiments of the invention, the region of interest 50, and therefore, the observation volume, is selected to be that volume, that is ejected from the droplet generating device in a subsequent ejection.

Regardless of the specific definition of the region of interest, in embodiments of the invention, measurement of the distribution of the cells/particles in the region of interest is performed to predict the number of cells/particles in the next droplet to be expelled from the orifice. This prediction based on the measurement performed prior to each droplet release may be used to control the apparatus in the inventive manner.

According to embodiments of the invention, the ability to detect and analyze single cells or particles is enhanced by aligning cells or particles one by one to flow across the sensing area of the region of interest. To this end, the fluid flow focusing section 54 of FIG. 2 is provided reducing the channel geometry so that its cross-section of flow has dimensions (size/width) in the order of the diameter of the cells or particles, generally slightly larger than the diameter of the cells or particles. Thus, the cells or particles can be made flowing in single file, i.e. one by one, through the single cell detection section 56.

Figure 3:
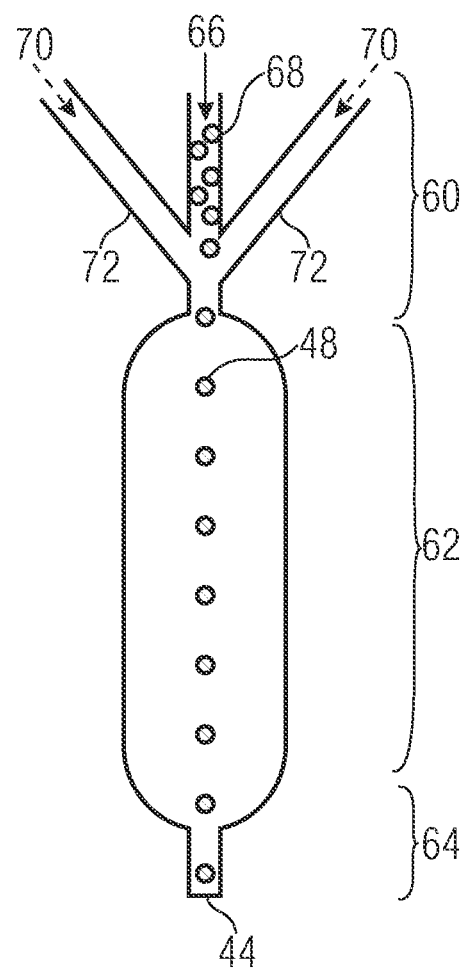
FIG. 3 is a schematic view of another embodiment of an output portion of a droplet generating device.

An alternative embodiment for an integration of a flow focusing effect with a droplet generating device is shown in FIG. 3. The droplet generating device comprises a flow focusing portion 60, a droplet generating portion 62 and an orifice portion 64 having an orifice 44. A cell or particle suspension 66 is supplied through a central channel 68 and sheath flows 70 for hydrodynamic focusing are supplied through side channels 72. By such an arrangement, the fluid flow may be squeezed by utilizing hydrodynamic flow focusing so that a stream comprising dimensions in the order of magnitude of the cell or particle diameter is formed, and therefore, cells 48 flow one by one through the droplet generating portion 62 and the orifice portion 64. In the embodiment shown in FIG. 3, the region of interest may be arranged somewhere along the droplet generating portion and the orifice portion, advantageously as close as possible to the orifice 44.

In still other embodiments, dielectrophoresis techniques may be used to make cells or particles flow in a single file.

Conventional actuators (not shown in FIGS. 2 and 3) may be arranged at an appropriate position, such as in the droplet generating portion 62, to effect ejection of a free flying droplet out of the orifice 44 upon actuation thereof.

The device for detecting, such as the camera, and the droplet generator may be controlled by a suitable control system, such as controller 30, which may be implemented in an appropriate manner by hardware or software. Generally, the control system may be implemented using an appropriate computing device including software and appropriate algorithms such that droplet ejection can be triggered depending on the results of the measurement performed by the device for detecting inside the region of interest. Generally, the position to which a droplet is ejected, depends on the results of the measurement. In embodiments of the invention, if the measurement shows that just one cell or particle will be ejected by the next ejection, the droplet is ejected to a first position, and if the measurement shows that another number of cells or particles will be ejected in the next ejection, the droplet will be ejected to a second position, such as a waste reservoir.

Generally, information on the cells or particles may comprise at least one of the presence of cells or particles, the number of cells or particles and/or any specific property of cells or particles. Specific properties of cells or particles may include the size or the color of cells or particles, for example.

Figure 4:
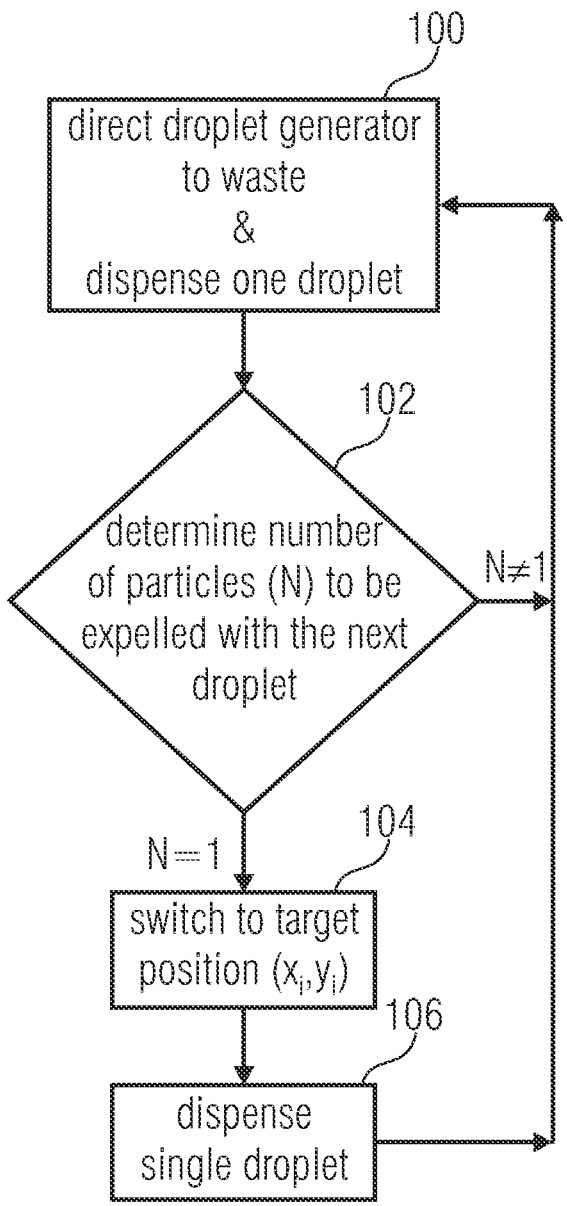
FIG. 4 is a diagram of an embodiment of an inventive method.

An embodiment of an algorithm to enable controlled release of droplets with one cell/particle per droplet is shown in FIG. 4.

After filling the droplet generator with a suspension including cells, such as living cells or particles, the droplet generator is triggered to dispense one droplet in step 100. During this dispension, the means for directing is controlled such that the droplet ejected is delivered into a waste reservoir. For this purpose, any suitable means of mechanical positioning, a mechanical shutter or an electrical or pneumatic deflection of the droplets as explained below with respect to FIGS. 5 to 8, may be used. Thereafter, in step 102, for every droplet the status of the cell/particle distribution inside the region of interest, i.e. the observation region, is recorded and the number of cells that will be expelled within the next droplet is predicted. In this embodiment, the number of cells/particles inside the region of interest is the measure to determine the number of cells/particles to be dispensed with the subsequent droplet. Moreover, in this embodiment the number of cells/particles inside the region of interest is the information, based on which the decision is made to which position the droplet is ejected. In embodiments of the invention, the number of cells in the region of interest can be easily obtained from a camera image by automatic image processing software to yield the measurement result, i.e. the number of cells/particles within the droplet to be dispensed next, N=0, 1, 2 . . . . If the measurement of the cell/particle distribution inside the region of interest yields exactly one particle to be expelled by the subsequent dispense, i.e. N=1, the repeated dispensing of droplets to the waste position is stopped and the next droplet is delivered to a target position by triggering a single droplet ejection. To do so, the droplet delivery has to be switched from the waste position to the target position by the means for directing, which may be referred to as switching means. Depending on the technical solution for this switching process, either a shutter has to be opened, a pneumatic/electrical deflection mechanism has to be stopped, the droplet generator has to be moved from the waste position to the target position by a mechanical movement, or target carriers have to be moved to align the target position with the droplet generator. This is indicated in step 104 as switching to the target position $(x_i, y_i)$. Thereupon, a single droplet including a single cell/particle is dispensed in step 106. If it is determined in step 102 that the number of cells/particles within a droplet is different from 1, the algorithm jumps back to step 100 and the next droplet is ejected to the waste position.

Once the droplet containing the single cell has been delivered to the target position in step 106, the algorithm starts again from the beginning. If the concentration of the cell suspension is properly chosen the number of droplets delivered into the waste position during one iteration can be small, such as 0 to 6, and the yield of droplets delivered to the target may be larger than 50% in average. Given a high dispensing frequency achievable with typical droplet generators, such as f>1000 Hz, and provided that the camera, deflection mechanism, control software and mechanical stages are fast enough, droplets populated with single cells can be printed with frequencies in the order of several hundred Hz enabling various printing and manipulation applications at reasonable throughput.

Experiments have been made by printing single yeast cells onto a Agarose gel with the described method. To be more specific, single *S. cerevisiae* cells have been printed on culture media. The experiment showed that single cells can be printed with high reliability using the inventive approach.

Specific implementations of means for directing ejected droplets to different positions are explained below referring to FIGS. 5 to 7. The means for directing may be configured to direct the generated droplets into a specific position for (i) discriminating respectively sorting different cells or particles and (ii) collecting target cells or particles into prescribed locations (iii) printing of two or three dimensional cell patterns with single cell resolution.

Figures 5A, 5B:
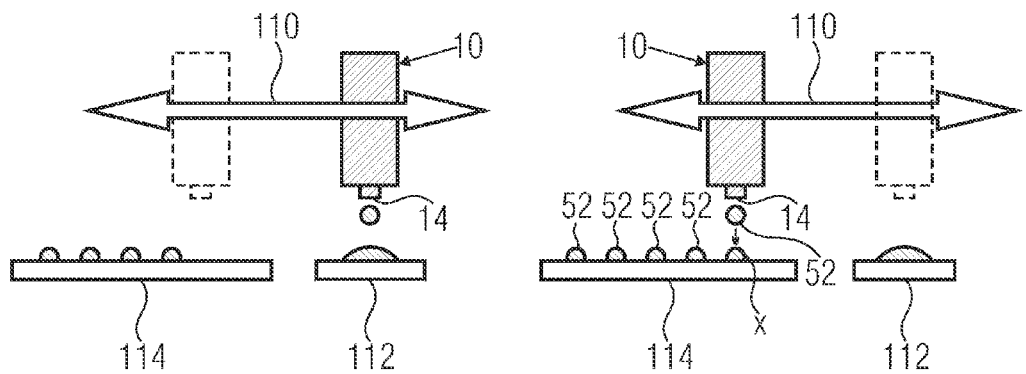
FIGS. 5a and 5b are schematic views of an embodiment of means for directing an ejected droplet to a first position or a second position.

In embodiments of the invention, a linear motorized stage comprising at least one axis that provides precise translational movement can be used for locating the droplet generator 10, and therefore, the orifice 14 at predefined positions. In FIGS. 5a and 5b, such a motorized stage is schematically indicated by an arrow 110. According to FIG. 5a, stage 110 is controlled to locate the droplet generator 10 above a first position 112, which may represent a waste position, such as a waste reservoir. According to FIG. 5b, the stage 110 is controlled to locate the droplet generator 10 above a target carrier 114, such that a droplet 52 is ejected to a desired target position x on the target carrier 114. As can be derived from FIGS. 5a to 5b, the droplet generator can be moved with respect to the target carrier 114 such that single droplets 52 can be ejected to a plurality of desired target positions such as to provide for an array of droplets, and therefore, cells on the target carrier 114. Thus, in the embodiment of FIGS. 5a and 5b, directing the droplets is accomplished by switching the droplet at least between two defined positions, i.e. a waste position and a single, or as shown in FIGS. 5a and 5b, multiple target positions.

Figures 6A, 6B:
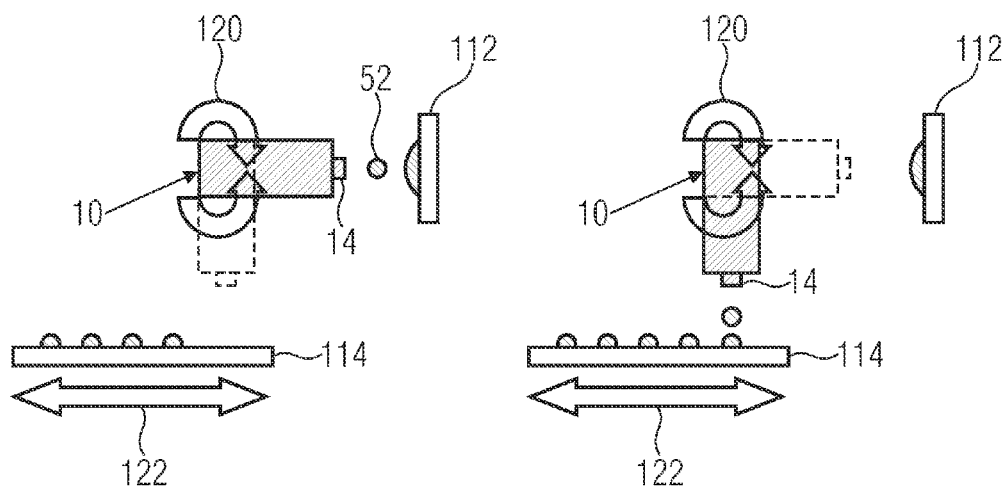
FIGS. 6a and 6b are schematic views of another embodiment of means for directing an ejected droplet to a first position or a second position.

Another embodiment is shown in FIGS. 6a and 6b. According to this embodiment, the droplet generator 10 is rotatably mounted as indicated by arrows 120. The droplet generator may be rotatable around an axis of rotation which is located at an end or a center of the droplet generator device. The rotation may be effected by any suitable mechanical, electrical or pneumatic means. As shown in FIGS. 6a and 6b, two defined positions may be used for dispensing droplets 52. In FIG. 6a, the droplet generator is positioned to eject droplets 52 to a position 112, which may be a waste position. A continuous dispensing of droplets may be generated with the droplet generator directed to position A to release undesired cells or particles until the device for detecting recognizes one or more cells or particles having a desired property. Upon generation of a corresponding detection signal, the droplet generator is rotated to a position shown in FIG. 6b, so that orifice 14 is brought into a position to eject droplets to a target position on the target carrier 114, to release the selected cell or particle. A motorized linear stage as indicated by arrows 122 may be provided to effect a translation movement of target area 114 so that the droplets can be ejected to different target positions on the target carrier 114.

Figure 7A:
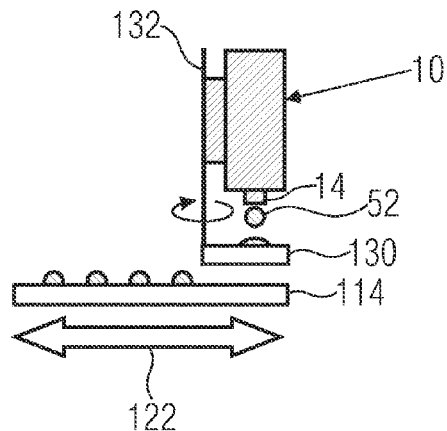
FIGS. 7a and 7b are schematic views of another embodiment of means for directing an ejected droplet to a first position or a second position.
Figure 7B:
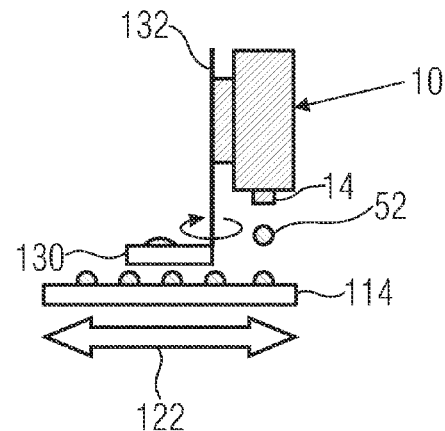

FIGS. 7a and 7b show another embodiment, in which means for directing comprises a mechanical shutter 130. The mechanical shutter 130 is rotatable about an axis 132 so that the shutter 130 can be positioned between the orifice 14 and the target carrier 114 as shown in FIG. 7a, and can be removed from a space between the orifice 14 and the target carrier 114, as shown in FIG. 7b. Again, a motorized linear stage 122 configured to move the target carrier 114 may be provided. As long as a desired property of cells or particles is not detected, the shutter 130 is controlled to be in the position shown in FIG. 7a, and droplets 52 are ejected to the shutter 130, which may be a waste position. Upon detection of a desired property, the shutter 130 is moved into the position shown in FIG. 7b and a droplet 52 having a cell/particle with the desired property is ejected onto the target carrier 114. Thus, in this embodiment, a mechanical shutter is used to block undesired droplets not containing cells/particles having the desired property, such as containing none or more than one cell or particle.

Figure 8A:
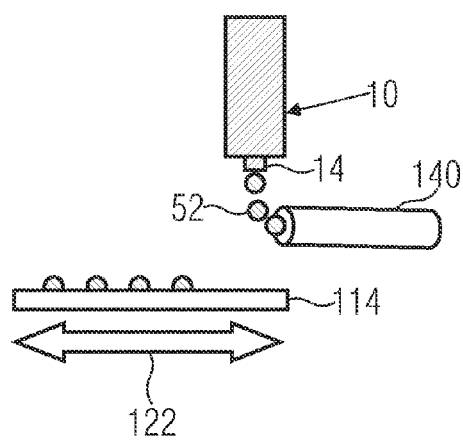
FIGS. 8a and 8b are schematic views of a further embodiment of means for directing an ejected droplet to a first position or a second position.
Figure 8B:
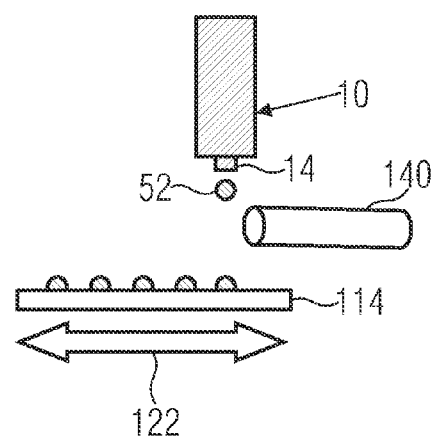

FIGS. 8a and 8b show an embodiment of a device for directing comprising pneumatic suction means. To be more specific, a pneumatic suction manifold 140 situated adjacent to the orifice 14 of the droplet generator 10 is provided to suck droplets carrying undesired cells or particles. Suction mechanism can be generated by connecting the manifold to a vacuum pump or a device that creates pressure below the atmospheric pressure. A negative pressure gradient between the manifold and ambient causes the droplets to be deflected into the manifold as shown in FIG. 8a. Thus, droplets containing undesired cells or particles can be directed into the manifold, which may represent a waste position. Once the sensor detects the target cell or particle, the suction mechanism of the manifold 140 is deactivated and the selected cell or particle is ejected to the prescribed position on the target carrier 114. Again, a motorized linear stage 122 may be provided.

It goes without saying that the motorized linear stage may be configured to provide for at least a two-dimensional movement of the target carrier in order to permit for dispensing droplets onto the target carrier in a two-dimensional pattern. In embodiments of the invention, the droplet generator can be implemented by any suitable means appropriate to eject droplets on demand. In embodiments of the invention, droplets on demand for the described purpose can be generated utilizing mechanical membrane actuation, thermal bubble-jet actuation, external pressure driven systems with micro-valve controls or any dispenser that can produce micro droplets. Examples of droplet generating devices may include commercial inkjet printers, dispensers known under trademarks NanoJet and PipeJet, or dispensing valve technologies.

In embodiments of the invention, a single-cell or particle detection for recognizing or analyzing and/or sorting the target cell or particle may be performed from a continuous cell or particle stream by using optical or impedance sensing means that are located within the region of interest. The sensing elements can be embedded within the droplet generator using an electrode pair fabricated along the sidewalls or on the channel, a wave-guide apparatus with a photo detector, or using an externally mounted vision system as a sensing device.

In embodiments of the invention, a reservoir may be incorporated into the apparatus in order to provide the suspension to the droplet generator. The reservoir may include means to keep the cells or particles in suspension and to supply the cells/particles to the droplet generator under controlled temperature and ambient conditions during the course of the cell/particle deposition process. In order to maintain a homogeneous state of the suspension, the reservoir may be integrated with a micro-mixer, a micro-agitator or any means to prevent cell or particle sedimentation from occurring.

Embodiments of the invention may comprise a x, y, z-motion control system with suitable interfaces for computer controlled printing of patterns.

Embodiments of the invention provide for the possibility of sorting of heterogeneous mixtures consisting of different droplets/particles. Due to the fact that the measurement means, such as the camera, may be applied to detect the status of the cells/particles in the region of interest prior to every dispensing event, the output of the measurement means may also be used to determine certain cell/particle properties. An example is determining the size of particles recorded by a camera through suitable image processing algorithms. Appropriate image processing algorithms are known to persons skilled in the art and therefore, do not need to be further explained here. Accordingly, cells/particles of different size can be easily sorted by printing them to different locations, such as into different wells of a micro well plate. To this end, the droplet generator may be moved to different positions by a mechanical stage, as explained above with respect to FIGS. 5a and 5b. Alternatively, a target carrier may be moved relative to the droplet generator. In embodiments of the invention, the droplet generator may be directed to a waste position as a default position and the position may be switched to a desired target position upon detection of a certain cell/particle property.

In embodiments of the invention, more sophisticated sorting applications can be performed by discriminating stained or fluorescently labeled cells according to their color. Techniques for surface marking and labeling known from FCM could be applied in the same manner to enable similar sorting capability as known from FCM. Also sorting according to impedance properties of the cells can be adopted in case an impedance sensor is used. Basically, any property can be considered for sorting that can be detected by a corresponding device for detection.

In embodiments of the invention, several measurement means may be combined to yield a higher information content of the cell/particle under consideration. For example, optical images obtained by a camera could be evaluated in combination with impedance measurement results to determine size and shape of the cell as well as its electrical properties simultaneously. A wealth of novel applications could be realized in this way.

In summary, embodiments of the invention provide for a device for dispensing single living cells or particles confined in a free flying micro droplet comprising at least one droplet-generating device supplied by a suspension of cells or particles to produce droplets on demand from the suspension out of at least one orifice. At least one measuring means may be provided to detect the presence and/or number and/or specific properties of cells or particles inside the droplet-generating device prior to ejection of a droplet. A motorized stage or other suitable mechanical, electrical, magnetic or pneumatic means may be provided, to direct droplets either to the target or to a waste reservoir depending on the detection result. An operating control mechanism by means of software, algorithms and a user-interface module may be provided to control the droplet generator, the measuring means and the droplet directing means.

In addition, embodiments of the invention provide for a method for generating and depositing droplets containing one single cell or particle only comprising the steps of: Step 1: filling a droplet generating device with cell or particle suspension. Step 2: directing a droplet generator to a waste position and generating one droplet. Step 3: detecting status and/or properties of cells or particles in the region of interest inside the droplet generator by suitable measuring means. Step 4: if exactly one single cell or particle is detected in the region of interest that will be ejected with the subsequent dispense, directing the droplet generator towards the target position and triggering the droplet generator to release a droplet to the desired position on the target. Step 5: if no cells or particles or if more than one cell or particle is detected in the region of interest that will be expelled with the subsequent dispense starting over again at step 2.

In embodiments of the invention, cell or particle counting can be achieved by summing the number of single-cells or particles passing through the region of interest within a specific period of time. To harvest a known quantity of cells or to produce a secondary buffer suspension with a known number of cells, the counted cells can be dispensed directly on the collector's reservoir. Statistical evaluations on cell populations can be performed in this manner similar to conventional FCM methods.

In embodiments of the invention, characteristic property studies may be performed and database records may be kept. Intrinsic cell or particle properties like chemical content, cell state, cell type, DNA content etc., or extrinsic characteristics like viability, size, shape, etc., can be deduced from the recorded data acquired through the measurement means in the region of interest for subsequent analysis. Each set of the measurement signal can be correlated with the actual characteristic of cells or particles as determined through subsequent separate physical laboratory test and measurement. This signal excitation versus cell or particle characteristic can be used as database to develop specific algorithms or signal conditioning for sorting of target cells according to such properties.

Embodiments of the invention provide for sorting of cells or particles according to measured properties. On the basis of electrical, optical or other physical properties of cells or particles determined by the measurement means, sorting algorithms can be defined to deliver the cells to distinct positions, such as different wells of a multi well plate. The considered properties can be included into the sorting algorithm to sort cells or particles according to their stipulated properties and deposit the selected cells or particles at prescribed positions.

By this, homogeneous cell populations of a known number of cells can be readily established.

Each deposited cell or particle possesses known individual properties, which may be recorded into a data storage device and which are retrievable for further analytical observation or analysis. The database may include the position of deposited cells together with a related properties profile. This database can be used to trace the temporal condition of an individual deposited cell or particle especially during post-harvesting analysis.

Depending on certain implementation requirements, embodiments of the invention can be implemented in hardware or in software. The implementation can be performed using a digital storage medium, for example a floppy disk, a DVD, a CD, a ROM, a PROM, an EPROM, and EEPROM or a FLASH memory, having electronically readable control signals stored thereon, which cooperate (or are capable of cooperating) with a programmable computer system such that the respective method is performed. Some embodiments according to the invention comprise a data carrier having electronically readable control signals, which are capable of cooperating with a programmable computer system, such that one of the methods described herein is performed. Generally, embodiments of the present invention can be implemented as a computer program product with a program code, the program code being operative for performing one of the methods when the computer program product runs on a computing device such as a computer. The program code may for example be stored on a machine readable carrier.

The above described embodiments are merely illustrative for the principles of the present invention. It is understood that modifications and variations of the arrangements and the details described herein will be apparent to others skilled in the art. It is the intent, therefore, to be limited only by the scope of the following claims and not by the specific details presented by way of the description and explanation of the embodiments herein.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. An apparatus for dispensing one or more cells or particles confined in a free flying droplet, comprising:
    a piezo driven on-demand droplet generating device configured to eject out of an orifice a free flying droplet of a suspension of cells or particles, said droplet generating device comprising a branch-less one-way channel comprising the orifice opening at one end thereof;
    a device for detecting information on cells or particles located in an observation volume of the suspension within the branch-less one-way channel; and
    director for directing an ejected droplet to a first position or a second position depending on the detected information; wherein
    the piezo driven on-demand droplet generating device includes a mechanical membrane adjoining a pressure chamber and a piezoelectric actuating device configured to actuate the mechanical membrane to reduce a volume of the pressure chamber to eject the free flying droplet on-demand.

2. The apparatus of claim 1, wherein the observation volume is a volume of the suspension which is located adjacent to the orifice and which is ejected as a free flying droplet upon the next dispensing event.

3. The apparatus of claim 1, wherein the first position is a target position and the second position is a waste position.

4. The apparatus of claim 1, wherein the information on cells or particles comprise at least one of a presence, a number, a size, a color and/or an impedance of the cells or particles.

5. The apparatus of claim 1, wherein said directors for directing are configured to direct an ejected droplet to the first position if the detected information indicates that the ejected droplet will comprise a predetermined number of cells or particles and to direct and eject the droplet to the second position if the detected information indicates that the ejected droplet will not comprise the predetermined number of cells or particles.

6. The apparatus of claim 5, wherein the predetermined number is one.

7. The apparatus of claim 1, wherein said directors for directing comprise a motorized stage configured to move the droplet generating device or one or more carriers carrying the first and/or second position, and/or deflectors for pneumatically, electrically or magnetically deflecting the ejected droplet.

8. The apparatus of claim 7, wherein said directors for directing comprise a shutter comprising the second position and positioner for positioning the shutter between the droplet generating device and the first position and for removing the shutter from a space between the droplet generating device and the first position.

9. The apparatus of claim 1, wherein the droplet generating device comprises focuser for making the living cells or particles flow one by one through the observation volume.

10. The apparatus of claim 9, wherein said focuser comprise at least one of:
    a channel comprising a tapered cross-section towards the orifice; and
    a central channel and two side channels entering the central channel at opposite positions.

11. The apparatus of claim 1, wherein the device for detecting comprises at least one of an impedance sensor located within the droplet generating device and an optical sensor located within or external to the droplet generating device.

12. The apparatus of claim 1, comprising a reservoir fluidically coupled to the droplet generating device.

13. The apparatus of claim 1, comprising a device for moving the droplet generating device and a carrier supporting the first position in two or three dimensions relative to each other and a controller for controlling the device for moving such that printing of two-dimensional or three-dimensional patterns of cells or particles on the carrier may be achieved.

14. A method for dispensing one or more cells or particles confined in a free flying droplet, comprising:
    filling a piezo driven on-demand droplet generating device with a suspension comprising cells or particles, the droplet generating device comprising a branch-less one-way channel comprising an orifice at one end thereof;
    detecting information on cells or particles located in an observation volume of the suspension within the branch-less one-way channel; and
    ejecting a droplet out of the orifice to a first or second position depending on the detected information; wherein
    the piezo driven on-demand droplet generating device includes mechanical membrane adjoining a pressure chamber and a piezoelectric actuating device configured to actuate the mechanical membrane to reduce a volume of the pressure chamber to eject the droplet on-demand.

15. The method of claim 14, wherein the information on cells or particles comprise at least one of a presence, a number, a size, a color and/or an impedance of the cells or particles.

16. The method of claim 14, comprising:
ejecting the droplet to the first position if the detected information indicates that the ejected droplet will comprise a predetermined number of cells or particles and to eject the droplet to the second position if the detected information indicates that the ejected droplet will not comprise the predetermined number of cells or particles.

17. The method of claim 16, wherein the predetermined number is one.

18. The method of claim 14 comprising counting a number of cells or particles passing through the observation region within a specific period of time based on the detected information.

19. The method of claim 14, wherein the detected information comprise a property of the cells or particles and wherein the method comprises sorting of at least two different types of cells or particles depending on the detected property by ejecting cells or particles comprising a first property to a first target location and cells or particles comprising a second different property to a second target location.

20. The method of claim 19, wherein the target locations are different wells of a multi-well plate.

21. A non-transitory computer readable medium programmed with a program code executable on a computing device, wherein the program code is effective to derive the information on cells or particles from an output of a sensor device and to control an apparatus for dispensing one or more cells or particles confined in a free flying droplet, to direct an ejected droplet to a first position or a second position depending on the derived information, the apparatus comprising:
  a piezo driven on-demand droplet generating device configured to eject out of an orifice a free flying droplet of a suspension of cells or particles, said droplet generating device comprising a branch-less one-way channel comprising the orifice opening at one end thereof;
  a device for detecting information on cells or particles located in an observation volume of the suspension within the branch-less one-way channel; and
  a director for directing an ejected droplet to a first position or a second position depending on the detected information; wherein
  the piezo driven on-demand droplet generating device includes a mechanical membrane adjoining a pressure chamber and a piezoelectric actuating device configured to actuate the mechanical membrane to reduce a volume of the pressure chamber to eject the free flying droplet on-demand; and
  the program code is executable to perform the steps of:
    detecting the information on cells or particles located in the observation volume of the suspension within the branch-less one-way control; and
    ejecting the droplet out of the orifice to the first or second position depending on the detected information.

* * * * *

UNITED STATES PATENT AND TRADEMARK OFFICE
CERTIFICATE OF CORRECTION

PATENT NO. : 8,834,793 B2
APPLICATION NO. : 13/707086
DATED : September 16, 2014
INVENTOR(S) : Peter Koltay et al.

It is certified that error appears in the above-identified patent and that said Letters Patent is hereby corrected as shown below:

In the Claims

The following should be corrected in Claim 14, column 14, line 67 as follows:

"…includes a mechanical membrane…"

The following should be corrected in Claim 21, Column 16, line 27 as follows:

"…one-way channel; and…"

Signed and Sealed this
Seventh Day of April, 2015

Michelle K. Lee
*Director of the United States Patent and Trademark Office*